(12) United States Patent
Wolozin et al.

(10) Patent No.: US 7,605,133 B2
(45) Date of Patent: *Oct. 20, 2009

(54) ISOLATED PEPTIDES TO TREAT ALPHA-SYNUCLEIN DISEASES

(75) Inventors: Benjamin Wolozin, Hinsdale, IL (US); Natalie Ostretova-Golts, Forrest Park, IL (US); Michael S. Lebowitz, Baltimore, MD (US)

(73) Assignee: Panacea Pharmaceuticals, Inc., Gaithersburg, MD (US)

( * ) Notice: Subject to any disclaimer, the term of this patent is extended or adjusted under 35 U.S.C. 154(b) by 314 days.

This patent is subject to a terminal disclaimer.

(21) Appl. No.: 10/909,116

(22) Filed: Jul. 30, 2004

(65) Prior Publication Data

US 2005/0032131 A1 Feb. 10, 2005

Related U.S. Application Data

(63) Continuation of application No. 09/901,187, filed on Jul. 9, 2001, now Pat. No. 6,780,971.

(60) Provisional application No. 60/279,199, filed on Mar. 28, 2001, provisional application No. 60/217,319, filed on Jul. 7, 2000.

(51) Int. Cl.
*A61K 38/08* (2006.01)
*C07K 7/06* (2006.01)
*C07K 9/00* (2006.01)

(52) U.S. Cl. .......................................... 514/16; 530/329

(58) Field of Classification Search ....................... None
See application file for complete search history.

(56) References Cited

U.S. PATENT DOCUMENTS 6,201,104 B1 * 3/2001 MacDonald et al. ........ 530/327

6,780,971 B2 8/2004 Wolozin et al. ............. 530/329
2003/0044838 A1 3/2003 Turnbough .................. 435/7.1

FOREIGN PATENT DOCUMENTS

| WO | WO-98/59050 | 12/1998 |
|----|-------------|---------|
| WO | WO 99/36081 | 7/1999 |
| WO | WO-00/18917 | 4/2000 |
| WO | WO-00/20020 | 4/2000 |

OTHER PUBLICATIONS

Souza et al (2000). FEBS Letters. 474,116-119.*
Accession No. AAB67386 (1997). Appendix b, pp. 1-2.*
Hashimoto, et al., "Oxidative Stress Induces Amyloid-like Aggregate Formation of NACP/Alphy-synuclein In Vitro," Neuro Report, Mar. 1999, vol. 10, No. 4, pp. 717-721.
Ostretova-Golts, et al., "The A53T Alpha-Synuclein Mutation Increases Iron-Dependent Aggregation and Toxicity," The Journal of Neuroscience, Aug. 15, 2000, vol. 20, No. 16, pp. 6043-6054.
Paik, et al., "Metal-Catalyzed Oxidation of Alpha-synuclein in the Presence of Copper (II) and Hydrogen Peroxide," Archives of Biochem and Biophys., Jun. 2000, vol. 378, No. 2, pp. 269-277.
Hashimoto, et al., "Role of Cytochrome c as a Stimulator of Alpha-Synuclein Agregation I Lewy Body Disease," Journal of Biol. Chem., Oct. 8, 1999, vol. 274, No. 41, pp. 28849-28852.
Database UniProt 'Online, Jan. 1, 1998 "Ylr269cp." XP002358527 retrieved from EBI accession No. UNIPROT: 013550.
Snyder, et al., "Magneisum Inhibition of Alpha Synuclein Aggregation" Abstacts of the society for Neuroscience, 27(1):1445, 2001.

* cited by examiner

*Primary Examiner*—Daniel E. Kolker
(74) *Attorney, Agent, or Firm*—Sterne, Kessler, Goldstein & Fox P.L.L.C.

(57) ABSTRACT

The present invention relates to drug screening methods and methods of preventing neural tissue damage caused by α-synuclein aggregation. These methods are especially useful in the design and development of inhibitors of Lewy body diseases and other synucleinopathies, and further useful in the treatment of such neurodegenerative diseases, particularly Parkinson's Disease.

12 Claims, 6 Drawing Sheets

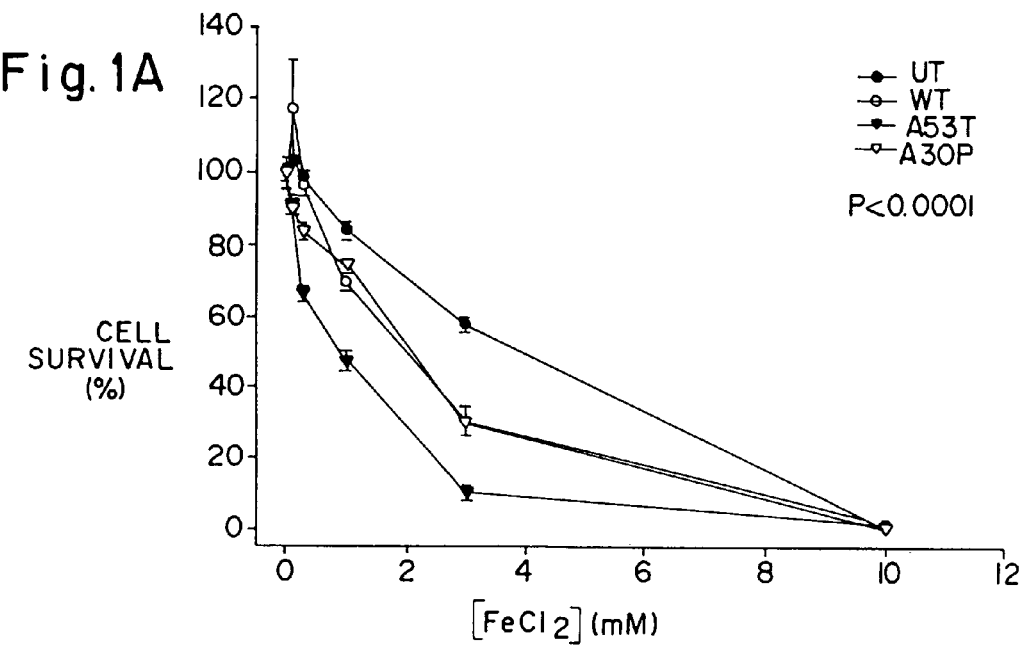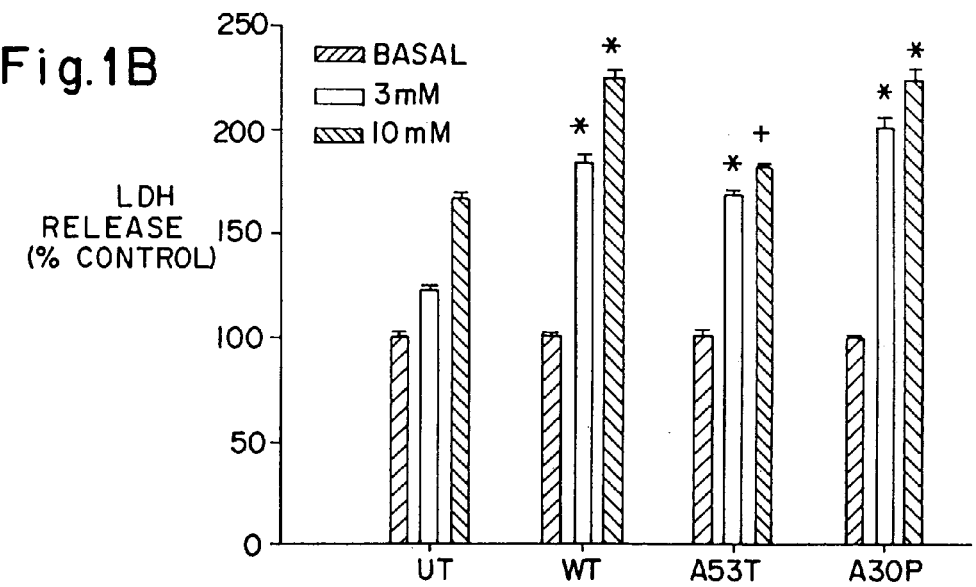

ISOLATED PEPTIDES TO TREAT ALPHA-SYNUCLEIN DISEASES

CROSS REFERENCE TO RELATED APPLICATIONS

This application is a continuation of, and claims priority to U.S. application Ser. No. 09/901,187, which was filed on Jul. 9, 2001 now U.S. Pat. No. 6,780,971. This application also claims benefit of U.S. Provisional Application Nos. 60/217,319 and 60/279,199, which were filed on Jul. 7, 2000 and Mar. 28, 2001 respectively.

FIELD OF THE INVENTION

The present invention relates to drug screening methods and methods of preventing neural tissue damage caused by α-synuclein aggregation. These methods are especially useful in the design and development of inhibitors of Lewy body diseases and other synucleinopathies, and further useful in the treatment of such neurodegenerative diseases, particularly Parkinson's Disease.

BACKGROUND OF THE INVENTION

Parkinson's disease (PD) is a common neurodegenerative disorder and was first described by James Parkinson in 1817. The four primary diagnostic signs of the illness are resting tremor, bradykinesia, muscular rigidity and postural instability. These signs of motor deficiency result from the loss of dopaminergic neurons in the nigrostriatal system [Gibb, W., et al., *J. Neurol. Neurosurg. and Psych.*, 51:745-52 (1988)].

PD is characterized by the formation of Lewy bodies and death of dopaminergic neurons. [Adams D. et al., *Principles of Neurology*, 874-880, 3rd Edition, McGraw-Hill, NY, (1985)]. The neuropathological hallmark of PD is the Lewy body. Lewy bodies are intracytoplasmic inclusions that occur in degenerating neurons which are composed of a dense core of filamentous and granular material surrounded by radically oriented filaments that have a diameter of 10-20 nm [Goedert, 20 M., et al., *Curr. Op. Neurobio.*, 8:619-32 (1999)]. In general, the causes of PD are not known and there has been vigorous debate over the relative roles of genetics and environmental factors [Tanner, C., et al., *JAMA*, 281:341-6 (1999)]. Exposure to manganese precipitated a Parkinson syndrome in miners which also includes schizophrenia form behaviors. Some epidemiological studies have found an association between industrial exposure to iron and the incidence of PD [Corell J. M et al., *Toxicol. Appl. Pharmacol.*, 80:467-72, (1985)], between incidence of PD and blood mercury levels. [Ngim C. H. et al., *Neuroepi.*, 8(3):128-141 (1989)] and with death rates from PD and proximity to iron related industrial processed [Rybicki A. et al., *Mov Disord.*, 8(1):87-92 (1993)].

α-Synuclein was originally identified as a protein that is upregulated associated with neuron outgrowth during the critical period of Zebra finch song learning [George M., et al., *Neuron*, 15:361 (1995)]. α-Synuclein is a ubiquitous protein that shares significant physical and functional homology to the protein chaperone, 14-3-3, and is particularly abundant in the brain (Ostrerova N. et al, *J. Neurosci.*, 19:5782 (1990); Clayton D. et al., TINS 21:249 (1998)]. α-Synuclein is normally phosphorylated at serines 87 and 129. (Okochi M. et al, *J. Biol. Chem.*, 275:390 (2000)]. Recent studies showed that mutations in α-synuclein can cause familial PD and that α-synuclein accumulates in Lewy bodies. These discoveries suggest that α-synuclein participates in the pathophysiology of PD. (Spillantini M. et al., *Nature*, 388:839 (1997); Spillantini M. et al, *PNAS USA*, 95:6469 (1998); Jenner P. et al, *Ann. Neurol.*, 44:S72 (1998)]. The only identified mutations associated with familial PD to date are the A53T and A30P mutations in the α-synuclein gene (Goedert, M., et al., *Curr. Op. Neurobio.*, 8:619-32 (1999); Papadimitriou, A., et al, *Neurology.*, 52:651-4 (1999); Polymeropoulos, M., et al, *Science*, 276:1197-9 (1997)]. However, there has been much circumstantial evidence implicating oxidative stress in the etiology of the disease (Jenner, P., et al., *Annual Neurol.*, 44:S72-84 (1998)].

A variety of experimental evidence suggests that Lewy bodies interact with α-synuclein. For example, immunohistochemical studies indicate that Lewy bodies stain strongly for α-synuclein and ubiquitin (Jenner, P., et al., *Annual Neurol.*, 44:S72-84 (1998); Markopoulou, K., et al., *Annual. Neurol.*, 46:374-81 (1999); Spillantini, M., et al., *Nature*, 388:839-40 (1997); and Spillantini, M, et al., *Proc. Natl. Acad. Sci. USA*, 95:6469-73 (1998)]. In vitro experiments using recombinant protein suggest that the mutations, A53T and A30P, increase α-synuclein aggregation in comparison with the wild type α-synuclein (Conway, K., et al., *Nature Med.*, 4:1318-20 (1998); Giasson, B., et al., *J. Biol. Chem.*, 274:7619-22 (1999); Hashimoto, M., et. al., *Brain Res.*, 25 799:301-6 (1998)].

One of the important questions regarding α-synuclein aggregation and Lewy body formation is whether these processes harm the cell. Lewy bodies could either be inert tombstone markers that occur in response to free radical damage, or they might be toxic agents that harm the cell. Examples of both situations exist in the literature. Aggregated amyloid-β (Aβ) is toxic to neurons, while lipofuscin appears to be innocuous to cells (Behl, C., et al., Cell 77:817-27 (1994)]. The Huntington's protein presents an intermediate situation where the toxicity associated with Huntington's appears to precede aggregation, and aggregation of Huntington's protein might even be protective [Saudou, F., et al., Cell 95:55-66 (1998)]. Our own previous studies showed that transient overexpression of α-synuclein is toxic to a variety of cells, including two neuronal cell lines, SK-N-SH and PC12 [Ostrerova, N., et al., *Neurosci.*, 19:5782-91 (1999)]. Consistent with this observation, Masliah and colleagues have recently shown that mice over-expressing α-synuclein show an age-related loss of dopaminergic terminals and motor impairment, which could be indicative of toxicity [Masliah, E. et al., *Science* 287:1265-1269 (2000)]. These findings suggest that an increased rate of α-synuclein aggregation might contribute to the mechanisms of neurodegeneration in PD and other Lewy body diseases.

Recent studies on transgenic animals also suggest that aggregation of α-synuclein is harmful to neurons. It was recently reported that dopaminergic dysfunction occurred in transgenic mice expressing wild type human α-synuclein [Masliah, E., et at., *Science* 287:1265-1269 (2000)]. Further, it was reported that *Drosophila* over-expressing α-synuclein exhibited dopaminergic dysfunction and dopaminergic neuronal death associated with development of α-synuclein aggregates [Feany, MB, et al., *Nature* 404:394-8 (2000)]. Evidence suggests that neurons with dopamine develop α-synuclein aggregates and degenerate as these aggregates development.

Recently, oxidative stress produced by iron and hydrogen peroxide has been shown to induce amyloid-like aggregate formation of α-synuclein in vitro [Hashimoto, M., et at., *NeuroReport.*, 10:717-21 (1999); Paik, S., et al., *Biochem. J.*, 340:821-8 (1999)]. Oxidative stress is thought to contribute to PD because dopamine, which is a strong free radical generator, is the principle neurotransmitter in the substantia nigra

[Chiueh, C., et at., *Adv. Neurol.*, 60:251-8 (1993); Jenner, P. et al., *Ann. Neurol.*, 25 44:S72-84 (1998)]. In addition, iron, which also stimulates free radical production, accumulates in the substantia nigra with age [Jenner, P., et al., *Ann. Neurol.*, 44:S72-84 (1998)]. Iron is deposited as hemosiderin granules in the cytoplasm, and mitochondria filled with ferritin granules have been observed in the neuronal and glial cells of the ventorlateral thalamus, caudate and lenticular nuclei and substantia nigra of Parkinsonian brains. [Earle M., *J. Neuropathol. Exper. Neurol.*, 27(1):1-14, (1968); Asenjo A. et al., *Rev. Neurologigue.*, 121 (6):581-92, (1969); Riederer P., et al., *J. Neurochem.*, 52(2):515-20, (1989)]. Thus, the oxidative conditions present in the substantia nigra could promote α-synuclein aggregation. However, in the prior art, whether such oxidative conditions actually promote α-synuclein aggregation in living neurons is unknown.

A need, therefore, exists for substances that will inhibit Lewy body formation, which can be used to treat diseases such as PD. At the same time, ways to find such substances, through screening assays, are also needed in the art. U.S. Pat. No. 6,184,351, discloses that synuclein aggregation can be induced by continually shaking α-synuclein for long periods of time at very high concentrations. However, the required high concentration and continuous shaking is neither physiologic nor conducive to the development of screening assays. Moreover, the assay described in the '351 patent does not directly measure α-synuclein aggregation; rather the soluble, unaggregated protein is determined. Further, the '351 assay is directed only to detecting nucleation-affecting agents, and not agents that would inhibit aggregation by other mechanisms. Therefore, the art would benefit from better methods for screening drugs useful for the inhibition of Lewy body formation.

SUMMARY OF THE INVENTION

The present invention relates to methods of identifying factors that lead to the inhibition of the aggregation of α-synuclein in vitro or in living neurons.

It is an objective of the present invention to provide a method of identifying, screening, and modeling pharmaceutical agents capable of inhibiting the aggregation pathway of α-synuclein. The pharmaceutical agents are, for instance, cations, small molecules, peptides, peptide mimetic compounds, nucleic acids, complex sugars, such as heparin analogues, or combinations thereof.

It is also an objective of the present invention to design, make, and use anti-α-synuclein aggregation drugs for treating a neurodegenerative condition, such as PD, Alzheimer's disease, diffuse Lewy body disease, mixed AD-PD, multiple system atrophy and Hallervorden-Spatz disease.

A & B.) BE-M17 cells over-expressing wildtype, A53T or A30P α-synuclein were treated with varying doses of $FeCl_2$ for 48 hrs and the viability was determined using the MTT assay (A) or the LDH assay (B).

C.) BE-M17 cells over-expressing wildtype, A53T or A30P α-synuclein were treated with varying doses of $H_2O_2$ for 48 hrs and viability was determined using the MTT assay. *p<0.001, +, p<0.01 by ANOVA analysis.

FIG. 2: Iron binds to α-Synuclein:

A.) $FeCl_2$ quenches the fluorescence emission spectrum by tyrosine in α-synuclein ($\lambda ex$=280 nm). High doses of iron (>10 mM) will quench tyrosine fluorescence, however proteins that bind iron exhibit quenching at much lower doses (presumably because the iron is kept near the tyrosine by the protein binding). Tyrosine has a fluorescence emission spectrum that has a peak emission of 310 nm when excited at 280 nm, respectively.

Figure 2A:
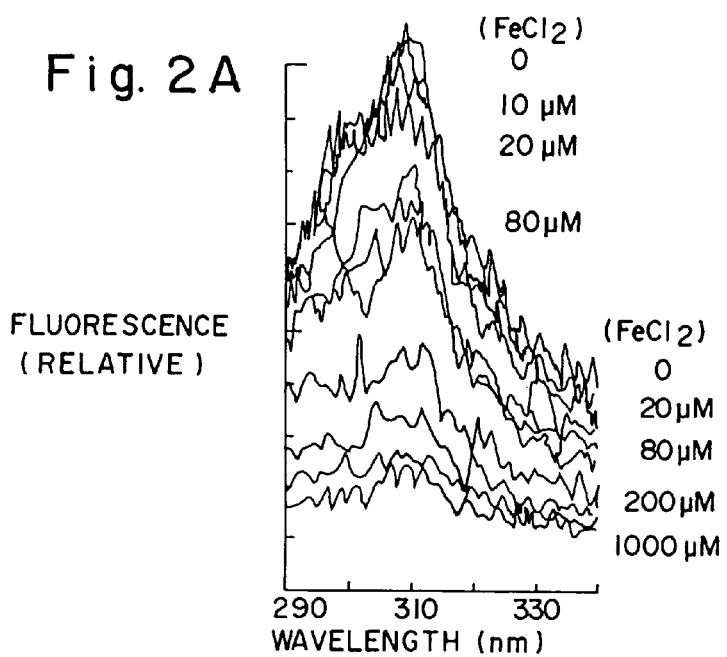
Figure 2B:
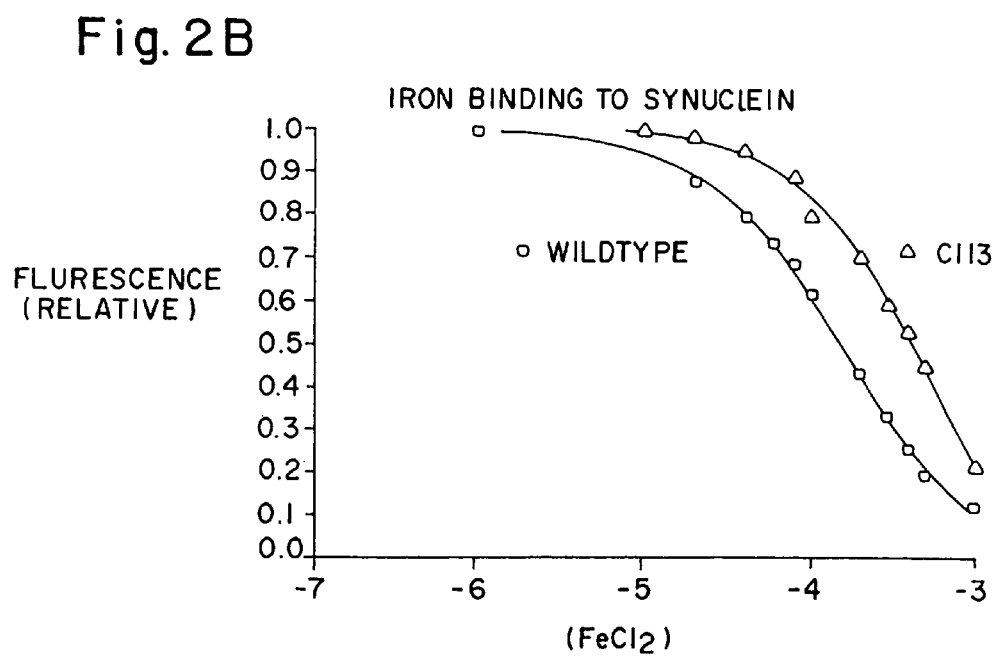

B.) Dose response curve for iron binding to wildtype and $\Delta C_{1-13}$ α-synuclein based on fluorescence emissions. A deletion construct lacking the last 27 amino acids of α-synuclein and analyzed binding of this construct. A C-terminal deletion construct of α-synuclein $\Delta C_{1-113}$ showed over a 4-fold reduction in iron binding, with an $IC_{50}$=726 µM (P<0.001) (FIG. 2B).

Figure 3A:
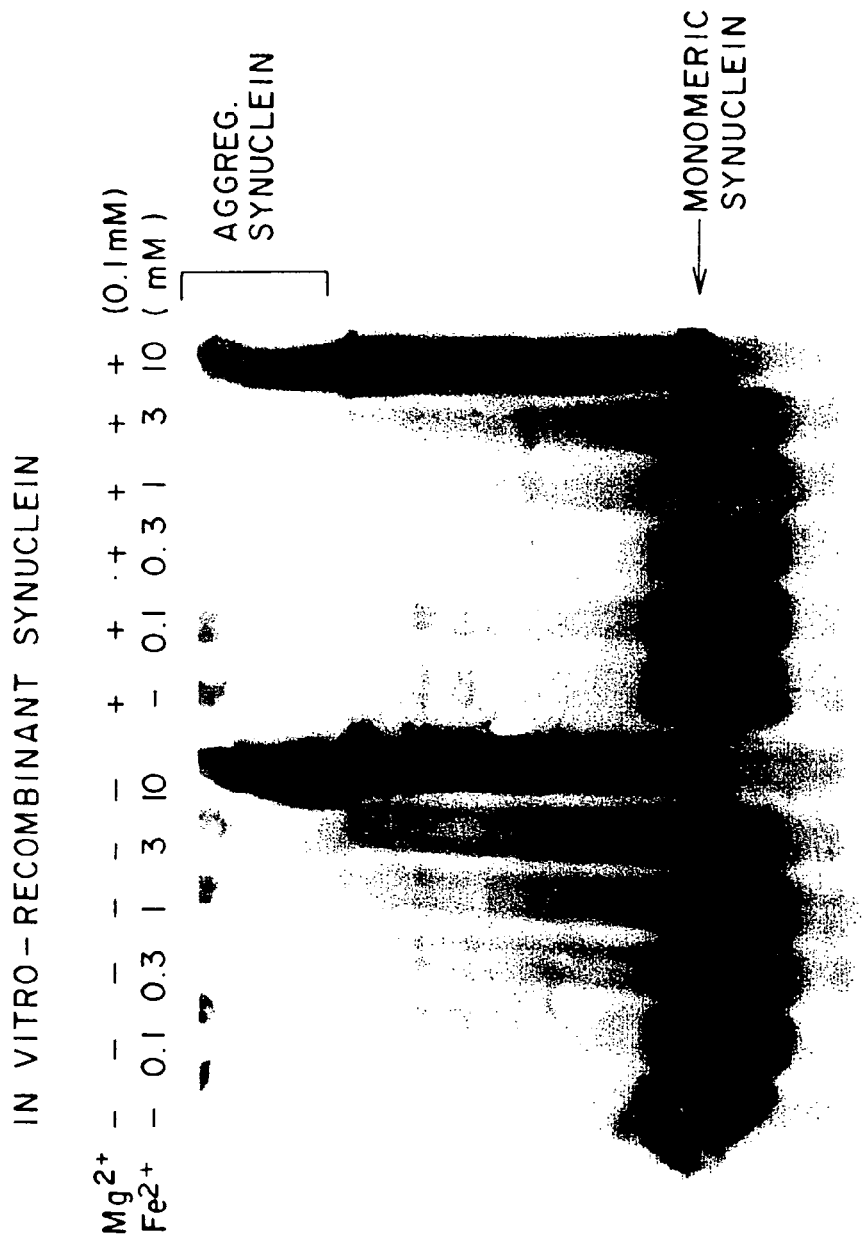

FIG. 3: Magnesium protects against synuclein aggregation.

A.) Magnesium converts α-synuclein to a conformation that resists aggregation.

B.) Magnesium inhibits α-synuclein aggregation. a.) Magnesium (0.1 mM) inhibits iron-induced aggregation of recombinant wild type α-synuclein (4 µM, 24 hr incubation). b.) Magnesium also induces α-synuclein aggregation in primary neurons. Higher doses are needed because the cell membrane poses a barrier to passage of the ions. Similar results are seen in BE-M17 cells over-expressing α-synuclein.

DETAILED DESCRIPTION OF THE INVENTION

Like many other proteins involved in neurodegenerative disease, α-synuclein has a high propensity to oligomerize/aggregate, forming the large protein filaments that are deposited in Lewy bodies. In vitro, α-synuclein tends to aggregate over a 3-day period. This rate is increased 2-3 fold in the mutant forms of α-synuclein, A53T and A30P. Metal ions, oxidative stress and other environmental factors may also increase this rate of aggregation (see below). The present invention is directed to the development of therapeutic agents that can inhibit α-synuclein oligomerization and thus Lewy body formation and neurodegeneration. Methods by which such agents may be readily identified are also contemplated by the present invention.

Thus, one aspect of the present invention relates to methods for determining whether an agent is useful in ameliorating the symptoms of a neurological disease that involves the aggregation of α-synuclein as part of its pathway, which measure the ability of the agent to prevent the aggregation of α-synuclein. One such method determines whether the agent is capable of inhibiting the aggregation pathway of α-synuclein, and comprises adding the agent to a sample containing α-synuclein in the presence of exogenous iron, and allowing the α-synuclein to aggregate, determining the amount, if any, of aggregation of α-synuclein, and then comparing that amount with an amount determined in a control sample in which the agent is absent. A decrease in the amount of aggregation indicates that the agent is capable of inhibiting the aggregation of α-synuclein, and thus that the agent would be useful in the treatment of the disease. The exogenous iron is added to induce aggregate formation. The range of iron concentration is about 0.1 to 1 mM, preferably 0.1 to 1 mM.

The above assay may be performed in vitro with α-synuclein, or in a cell culture system or animal model. For the in vitro assay, to a solution of α-synuclein (is) are added components that will accelerate aggregation, such as an exogenous source of iron or copper (for example, salts or metalloproteins), and/or free radical generators, for example dopamine and hydrogen peroxide. A mutant α-synuclein (A30P or A53T) which tends to have accelerated oligomerization may also be used. Concurrently, the agent to be tested is added, and sufficient time is allowed for aggregation to proceed. Typically, this is about 12 hours, although longer time periods may be observed.

There are several ways of detecting any aggregated α-synuclein, and the present invention is not limited hereby. One method exemplified herein employs SDS-PAGE and immunoblotting. α-Synuclein oligomers have been shown to be stable to SDS and, thus, oligomer-banding patterns can be identified on a blot. A second method of determining the extent of oligomerization is to stain the oligomers with thioflavine-S and visualize the filaments by fluorescence microscopy. Thioflavine-S binds to the β-pleated sheets that are formed upon oligomerization.

One may also use a novel fluorescence anisotropy assay for α-synuclein oligomerization that can be of great utility for higher throughput drug screening, and which is also a subject of the present invention. Fluorescence anisotropy is a measure of the rotational diffusion of a fluorophore in solution. Small molecules rotate more rapidly than larger complexes, thus as α-synuclein oligomerizes the fluorescence anisotropy of an associated fluorophore would be expected to increase. α-Synuclein can be specifically labeled on the N-terminus with an amine reactive fluorophore at neutral pH, which may be chosen from fluoroscein, pyrene and dansyl derivatives, for example. By monitoring changes in the anisotropy, one can readily determine compounds that can inhibit aggregation because they would be expected to block an increase in anisotropy. See Lakowicz, Joseph R., Principles of Fluorescence Spectroscopy, Chapter 5, pp. 111-153, Plenum Press (NY) (1986), which is incorporated herein by reference.

For a cell culture assay, neuroblastoma cells can be used, such as BE-M17 cells, which are publicly available from the ECACC. In order to induce α-synuclein aggregation in the cells, the cells are transfected with a vector that expresses α-synuclein or one of the mutant variants thereof (A30P or A53T), thereby upregulating the production of α-synuclein. This upregulation has the effect of inducing aggregation, which would not otherwise occur. As with the in vitro assay above, $Fe^{2+}$ with or without free radical generators (such as hydrogen peroxide and dopamine) is added to the cell culture, and the cells are monitored for intracellular oligomerization over a 12-96 hour period. The aggregation can be detected by, for instance, histochemical staining with thioflavine-S or labelled anti-α-synuclein antibodies. Alternatively, the cells could be harvested, lysed, separated on an SDS-polyacrylamide gel, and immunoblotted with labeled anti-α-synuclein antibodies. Another way to detect the aggregated α-synuclein is by using electron microscopy.

Preferably, one or more free radical generators, such as dopamine and hydrogen peroxide, are added together with the iron ($Fe^{2+}$) to the cell culture assays.

Most preferably, only $Fe^{2+}$ and hydrogen peroxide are added as the inducers of aggregation (but for cells with the A53T mutant, no free radicals are necessary).

By the term "labelled" is meant labelling with any substance typically used in biochemical assays of this sort, and includes, for example, radioactive, enzymatic, chemiluminescent, and fluorescent labels. Preferably, the label is enzymatic, and most preferably the label is a peroxidase.

In a cell culture assay using human BE-M17 neuroblastoma cells that over-express wildtype, A53T mutant or A30P mutant α-synuclein, the amount of aggregation occurring in the cells is dependent on the amount of α-synuclein expressed and the type of α-synuclein expressed, with the amount of α-synuclein aggregation following a rank order of A53T>A30P>wildtype>untransfected. In addition to stimulating aggregate formation, α-synuclein also appears to induce toxicity. BE-M17 neuroblastoma cells over-expressing α-synuclein show up to a 4-fold increase in vulnerability to toxicity induced by iron. The vulnerability follows the same rank order as for aggregation. These data suggest that α-synuclein acts in concert with iron and dopamine to induce the formation of Lewy body pathology in PD and cell death in PD.

In another aspect of the present invention is a method of inhibiting the formation of α-synuclein aggregates. More specifically, this method is for the 20' treatment of Lewy body diseases, such as Parkinson's disease, whereby Lewy body formation is controlled (or lessened) by inhibiting α-synuclein aggregation. That is, the present invention contemplates a method for treating a neurodegenerative disease that involves the formation of Lewy bodies, which comprises administering to a patient in need thereof one or more agents that inhibit the formation of α-synuclein aggregates, whereby the presence of Lewy bodies remains the same or, more preferably, is reduced. The particulars of such treatment depend on the therapeutic agent involved, the particular disease and its stage of progress, and other factors such as bioavailability, etc., which are all factors that the skilled practitioner can take into account when determining dosages, routes of administration, and length of treatment, and the present invention is not limited hereby.

In another aspect of the present invention are therapeutic agents for the treatment of Lewy body diseases, which have been discovered by the present inventors. In particular, the present inventors found that $Mg^{2+}$ inhibits the aggregation of α-synuclein. More specifically, the inventors found that both iron and magnesium bind to α-synuclein, but exert opposing actions on α-synuclein aggregation. Iron increases α-synuclein aggregation, whereas magnesium inhibits α-synuclein aggregation. In addition to decreasing aggregation of wildtype α-synuclein in cell culture, magnesium also decreases formation of visible neuronal inclusions and protects against neurotoxicity. These data are indicative of a therapeutic role for magnesium in the treatment of a Lewy body disease, such as PD, in which the progression of the disease can be at least slowed and likely reversed.

It is known that iron levels are increased in brains of patients with PD, whereas magnesium levels are reduced, but the role that these metals play in the pathophysiology of PD has never been elucidated. See, for instance, Durlach et al., *Magnes. Res.* 11:2542 (1998). The prior art does not suggest that regulating the balance of iron and magnesium in the brain would have an affect on Lewy body formation or disease progression. U.S. Pat. Nos. 4,985,256; 4,837,164; and 5,004,615 to Glick disclose administering magnesium to improve memory in dementias, among which is mentioned ALS-PD ("amyotropic lateral sclerosis and Parkinsonism complex") This is a disease recognized in Guam, and involves high levels of aluminum and low levels of magnesium in brain cells of those affected. However, the condition is very different from Parkinson's disease, particularly with respect to Lewy body formation, which is absent in ALS-PD. Moreover, The purpose for which Glick suggests supplementing magnesium is to raise magnesium to normal levels in the recited demtentias, not to interfere with α-synuclein aggregaton. It was not until the present invention that it was shown that magnesium has an affect on α-synuclein aggregation.

Therefore, as a preferred embodiment, $Mg^{2+}$ is administered to a mammal in need of treatment of a Lewy body disease. The $Mg^{2+}$ may be in any non-toxic, pharmaceutically acceptable form. Preferably, the magnesium is administered as magnesium sulphate, magnesium phosphate, magnesium gluconate, magnesium oxide, magnesium hydroxide, magnesium chloride, magnesium carbonate, or combinations thereof. For parenteral administration, most preferable is magnesium sulphate.

As used herein, the term "administration" refers to the application or delivery of a drug to a mammal. This term is intended to include any means of administration which accomplishes the application or delivery of drug, but preferred are those means of administration that target the magnesium to the brain tissue involved. The term is also intended to include any means necessary to accomplish such administration, such as a sugar loading procedure to enable a drug to cross the blood-brain barrier, if required.

The dosage of magnesium is determinable by the skilled practitioner, for instance by referring to treatment regimens of other conditions with magnesium salts. Magnesium should not be administered such that toxic levels are attained. The present inventors have found experimentally that the magnesium required to inhibit α-synuclein aggregation in vitro is within the range commonly employed in clinical protocols using magnesium (for example, eclampsia of pregnancy), i.e., 0.5-2 mM $MgSO_4$. Plasma levels in a normal adult human are between 1.5 and 2 mEq per liter, about one third of which is bound to protein. In hypermagnesemia, which is primarily due to renal insufficiency, excess magnesium results in results in depression of the central nervous system and the peripheral neuromuscular junction. When plasma levels begin to exceed 4 mEq per liter, deep tendon reflexes become decreased or absent, at which point respiratory paralysis is a risk. Therefore, in the treatment with magnesium salts in accordance with the present invention, appropriate monitoring of magnesium levels should be performed.

Magnesium salts have been used therapeutically in humans for years. For instance, many antacids are comprised of magnesium salts, specifically citrate and sulfate salts. Thus, such salts are contemplated as useful if administration of the magnesium is gastrointestinally. For parenteral administration (intramuscular or intravenous), which is preferred in the present invention because higher systemic levels can be attained, magnesium sulfate is the salt of choice. Such administration has for years been employed in the treatment of seizures associated with eclampsia of pregnancy, in which an initial and sustaining dosage, base on body weight, are given. See Flowers et al., *Obstet. Gyn.*, 19:315-327 (1962), the contents of which are incorporated herein by reference, for a dosage schedule for toxemia of pregnancy. Such a regimen is applicable to the treatment of a Lewy body disease according to the present invention as well, with plasma concentrations also within the 3-6 mg.% range. However, in the case of a progressive neurodegenerative Lewy body disease, such as PD, the regimen may span the remainder of life.

The present inventors also discovered that other agents useful for treating Lewy body diseases and synucleinopathies (diseases that have α-synuclein involved in their pathways, but not necessarily Lewy bodies) are peptides, or derivatives thereof, that bind to α-synuclein and inhibit the aggregation thereof. These peptides, alone or in composition, can be used to treat a subject with a neurodegenerative disease that displays Lewy body pathology. While not being bound by any particular theory, it is believed that the binding of the peptide(s) to α-synuclein somehow prevents the α-synuclein from aggregating, perhaps by interfering with the role of $Fe^{2+}$ in the aggregation.

Such peptides can be found, for instance, by using phage display to select for those phage expressing a peptide on their surface that binds to α-synuclein, and determining what the peptide is. The inhibitory effect of that peptide, or any peptide for that matter, can also be tested to determine its usefulness as an agent for treating a Lewy body disease or synucleinopathy by using assays such as those disclosed herein or as disclosed in U.S. Pat. No. 6,184,351, which is incorporated herein by reference. Such peptides have been selected for their ability to bind to the C-terminal (approx. amino acids 113-140), and the NAC portion (approx. amino acids 61-87) of α-synuclein, because this region is thought to be involved with the aggregation process. Several peptides that bind to the C-terminal portion are as follows (all peptides are given in 5' to 3' order) (1) WRQTRKD (SEQ ID NO: 1); (2) HYAKNPI (SEQ ID NO: 2); (3) ATINKSL (SEQ ID NO: 3); (4) RRRGMAI (SEQ ID NO: 4); (5) THRLPSR (SEQ ID NO: 5); and (6) TKHGPRK (SEQ ID NO: 6). Several peptides that bind to the NAC portion are: (1) SLKRLPK (SEQ ID NO: 7); (2) RLRGRNQ (SEQ ID NO: 8); (3) WPFHHHR (SEQ ID NO: 9); (4) HLYHHKT (SEQ ID NO: 10); (5) THIHHPS (SEQ ID NO: 11); and (6) MMMNMRL (SEQ ID NO: 12). The NAC portion was chosen because this piece of the protein has been found to aggregate in amyloid plaques in Alzheiiner's disease. Particularly preferred, because of stronger binding properties, are THRLPSR (SEQ ID NO: 5); SLKRLPK (SEQ ID NO: 7); THIHHPS (SEQ ID NO: 11) and MMMMMRL (SEQ ID NO: 12). Most preferred is the peptide SLKRLPK (SEQ ID NO: 7).

The peptides can be made by methods well known in the peptide synthesis art, and variants or analogs can also be made according to established principles. For example, one may wish to increase the therapeutic efficacy of the peptide, change the hydrophobicity/hydrophilicity, or reduce unwanted side effects. The peptide structure can be changed by the addition of functional groups, such as for targeting the compound to the neural tissues affected by the particular Lewy body disease. Also, substitutions of one or more amino acids of the peptide may be made, and these will typically involve conservative substitutions, i.e., substitutions that retain a property of the original amino acid, such as charge, etc. Examples of such conservative substitutions are ones made between (1) M, I, L and V; (2) F, Y, and W; (3) K, R, and H; (4) A and G; (5) S and T; (6) Q and N; and (7) E and D. The changes to the peptide need not be conservative; the altered peptide can always be tested for efficacy in aggregation inhibition by the assays mentioned previously.

Preferably, the peptides are resistant to proteolytic digestion. Such peptides can be made protease resistant by the presence of D-amino acids or by the replacement of susceptible peptide bonds with non-hydrolyzable bonds. Many such bonds, and how to introduce them, are known in the art. They include -psi[$CH_2NH$]— (reduced amide peptide bonds); -psi[$COCH_2$]— (ketomethylene peptide bonds); -psi[$CH(CN)NH$]— ((cyanomethylene)amino peptide bonds); -psi[$CH_2CH(OH)$]— (hydroxyethylene peptide bonds); -psi[$CH_2O$]— (peptide bonds); and -psi[$CH_2S$]— (thiomethylene peptide bonds). The peptides can also be constructed with end modifications, such as an amide at the C-terminus or an acetyl group at the N-terminus, which will make them resistant to proteolytic digestion.

Non-peptide (peptide mimetic) analogs are compounds in which one or more of the residues in the peptide is (are) replaced by a non-peptide moiety. The non-peptide moieties should allow the peptide to retain its natural, or more bioactive, conformation. See Nachman et al., Regul. Pept. 57:359-370 (1995) for methods to prepare nonpeptide mimetic compounds.

The peptides may be modified by conjugating them to a compound which facilitates their transport across the blood brain barrier. Such compounds, for example, may be selected from fatty acids, cationized antibodies or albumin, and the amphiphilic drug-oligomer conjugates disclosed in WO 00/09073, which is incorporated herein by reference. Alternatively, the peptides can be administered with a compound or compounds which facilitate transport across the blood brain barrier, but which is not conjugated to the peptide. For examples of such compounds, see U.S. Pat. Nos. 5,112,596 and 5,268,164, which are both incorporated herein by reference.

By the term "peptide" is meant any of the foregoing peptides and derivatives thereof, and is not limited in the number of amino acids. Thus, a "peptide" could include a polypeptide.

Compositions, particularly pharmaceutical compositions, comprising one or more of the peptides also form part of the present invention. A therapeutically effective amount of the peptide(s) (one which will ameliorate disease progression) may be combined with any pharmaceutically and/or physiologically acceptable carrier, such as aqueous solutions, salts, buffers, stabilizers, solubilizers, fillers, diluents, and other known substances, depending on the route of administration. The compositions may be prepared in any of a variety of forms suitable for the desired mode of administration. For example, pharmaceutical compositions may be prepared in the form of tablets, powders, lozenges, elixirs, suspensions, emulsions, solutions, syrups, aerosols (as solids or in liquid media), soft-gel and hard-gel capsules, suppositories, sterile injectable solutions, sterile packaged powders, and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like. Proper formulation is dependent upon the route of administration chosen. For injection, the agents of the invention maybe formulated into aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For oral administration, the compounds can be formulated readily by combining the active compounds with pharmaceutically acceptable carriers known in the art. The peptides may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. See Remington's Pharmaceutical Sciences, 18$^{th}$ Edition, Mack Publishing Co. (1990), which is incorporated in its entirety herein by reference, for a comprehensive list of formulations.

One or more of the peptides can be administered to a mammal in need of treatment of a Lewy body disease, in a manner conventionally employed and determined on an individual basis by the practitioner. Preferably, the peptides are administered by injection or gradual infusion over time. Other routes of administration that may be used are oral, intravenous, intracranial, intraperitoneal, intramuscular, intracavity, intrarespiratory, subcutaneous, transdermal, or liposome-mediated delivery. Delivery to specifically affected neuronal cells can also be accomplished using targeted delivery methods, which include conjugation to a molecule that selectively binds to the cells or envelopment in liposomes that contain a targeting molecule which will bind to the affected cells. Such methods for targeting are well known in the art, for instance in U.S. Pat. No. 5,391,723, which is incorporated herein by reference. In addition, some liposomes are commercially available.

In a preferred embodiment, concomitant administration of the peptide(s) with magnesium therapy as set forth above is envisioned. The combined therapy is likely to accelerate the recovery, and reach a more complete level of recovery. Once the recovery has reached the stage of an absence of further loss of clinical function, co-administration of magnesium may allow for a lower dose of peptide to be used for maintenance.

The subjects of therapeutic treatment may be humans, or animals such as rodents, dogs, cats, drosophila and C. elegans. Such animals may be useful human model systems.

Finally, kit for use in performing an assay to test the affects of various substances on the aggregation of α-synuclein, is also contemplated. The test would comprise at a minimum lyophilized α-synuclein, iron or copper salt, and a buffer, such as PBS or Tris buffer (at physiological pH). The kit could also comprise a free radical generator, such as dopamine or hydrogen peroxide. Preferably, the kit comprises iron chloride. For the free radical generator, hydrogen peroxide is preferred.

This invention is illustrated in the Examples that follow. These examples are set forth to aid in understanding of the invention but are not intended to, and should not be construed to, limit in any way the invention as set forth in the appended claims.

The following materials and methods were used in the examples herein.

Cloning, Overexpression, and Purification of α-Synuclein:

α-Synuclein (wildtype, A53T and A30P) was cloned into the NotI site of pcDNA3. The sequence of each construct was confirmed by DNA sequencing. For production of recombinant protein, α-synuclein was inserted into the NcoI/NotI site of the ProEx His 6 (SEQ ID NO: 13) vector (GIBCO/BRL). To generate recombinant α-synuclein, Bper (Pierce) reagent was used to solubilize the recombinant αsynuclein from the IPTG-induced bacterial lysates, which were then passed over a nickel-agarose affinity column, washed and eluted with imidazole according to the manufacturer's directions (GIBCO/BRL). Following purification, the His-6 tag (SEQ ID NO: 13) was cleaved with TEV protease and removed by passing through a nickel-agarose column. Antibodies used include: polyclonal anti α-synuclein (SC1, 1:2000 for immunoblotting and 1:500 for immunocytochemistry against human α-synuclein, residues 116-131, sequence =MPVDP-DNEAYEMPSEE) (SEQ ID NO: 14), monoclonal anti α-synuclein-1 (1:1000, Transduction Labs), polyclonal rabbit anti-ubiquitin (1:1000 for immunoblotting and 1:500 for immunocytochemistry, Dako).

Phage display: Incubating a library of phage that is all identical except for a sequence of 7 amino acids that are presented on the coat and randomly differ from phage to phage. Phage which express a sequence that specifically binds to α-synuclein are then isolated, cloned, and the DNA sequenced to determined the amino acid sequence. The 7 amino acid peptide is then synthesized and tested directly.

Cell Culture: Cells were grown in OPTIMEM (Gibco/BRL) supplemented with 10% FBS, non-essential amino acids, sodium pyruvate and 500 µg/ml G418, as needed. G418 was used for selection.

Immunoblotting: Cells were harvested with SDS lysis solution (2% SDS, 10 mM Tris, pH 7.4, 2 mM β-glycerol phosphate, 1 µM AEBSF). The amount of protein was determined using the BCA assay (Pierce), 5-30 mg per lane was run on 14% SDS polyacrylamide gels and transferred to nitrocellulose (200 mAmp, 12 hrs). The nitrocellulose was then incubated 1 hr in 5% milk/PBS, washed, incubated overnight in 1° antibody, washed, then incubated 3 hrs in peroxidase coupled 2° antibody and developed with chemiluminescent reagent (NEN).

Cell fractionation: For cell fractionation the cells were harvested in buffer containing 20 mM Tris, pH 7.4, 2 mM EDTA, 0.25 M sucrose, and 20 µg/mL protease inhibitor cocktail (Sigma). The cell lysate was sonicated and centrifuged at 100,000×g at 4° C. for 1 hr.

MTT and LDH toxicity assay: Cells were plated in 96 well dishes at 5000 cells/well in 100 µl growth medium. For the MTT assay, viability following 48 hrs of pharmacological treatment was analyzed by adding 0.5 mg/ml MTT (MTT, 3-[4,5-dimethylthiazol-2-yl]-2,5-diphenyltetrazolium bromide) and incubating at 37° C. for 3 hrs. Lysis buffer (100 µl of 20% SDS in 50% N,N-dimethylformamide) was then added and the plates are read at 540 nm after 24 hrs. For the lactate dehydrogenase (LDH) assay, viability following 24 hrs of pharmacological treatment was analyzed using MTS reagent and the Cytox 96 kit (Promega) according to manufacturer's directions.

Thioflavine-S Histochemistry: Cells were fixed 30 min in 4% paraformaldehyde. Following two PBS washes, the cells were incubated with 0.5% Thioflavine-S for 8 min, washed three times in 80% ethanol, washed once in $H_2O$ and then mounted.

Electron Microscopy: Cells were detached by scraping, spun down and fixed in 2% glutaraldehyde for 2 hrs at 4° C. and then post-fixed in 1% osmium tetroxide for 1 hr at 4° C. The samples were dehydrated, embedded in epoxy resin (Electron Microscopy Science, Fort Washington, Pa.), and cut into 70 nm sections for microscopy. The sections were then post-stained with 5% uranyl acetate, and Reynolds lead citrate. Samples were viewed with a Hitachi H-600 transmission electron microscope at 75 kV.

Iron Staining: Cells were fixed 30 min in 4% paraformaldehyde, followed by two PBS washes, stained using the Accustain® Iron Stain according to manufacturer's directions (Sigma).

Immunohistochemistry: For light microscopy, cells are fixed with 4% paraformaldehyde, washed, permeabilized by incubation for 30 min with 0.2% Triton-X100, blocked with 5% dry milk/1% goat serum/PBS, washed and then incubated overnight in 1° antibody (1:500). Development is with an ABC kit and 3',3'-diaminobenzidine as per manufacturer's directions (Vector, Burlingame, Calif.).

EXAMPLES

Example 1

Iron and Free Radicals Stimulate α-Synuclein Aggregation

To test whether A53T and A30P mutations in α-synuclein increase the tendency of α-synuclein to aggregate in neurons, α-synuclein aggregation was determined in human BE-M17 neuroblastoma cells that were stably transfected with wild type, A53T or A30P α-synuclein. Each cell line was treated for 48 hours with freshly prepared $FeCl_2$ (1 or 10 mM), then harvested, homogenized and fractionated into membrane and cytoplasmic components. The membrane (5 µg/lane) and cytoplasmic (20 µg/lane) components were immunoblotted with monoclonal anti-α-synuclein antibody.

Aggregates of α-synuclein were evident in the membrane fraction, but not in the cytoplasmic fraction. Treatment of the A53T-expressing cell line with $FeCl_2$ induced dose-dependent formation of heterogeneous high molecular weight-α-synuclein aggregates that migrated in the stacking gel. A large amount of anti-α-synuclein immunoreactivity was also apparent in the upper portions of the separating gel, in the range of 45-200 kDa. Because these bands are significantly larger than monomeric α-synuclein, which has a mass of 19 kDa, these bands might also represent α-synuclein polymers and aggregates. For instance, the bands at 38 and 57 kDa have sizes consistent with dimers and trimers of α-synuclein. Immunoblots done with a different antibody, a polyclonal anti-α-synuclein antibody, also showed aggregate production under the same conditions. Treatment of the other cell lines (untransfected, wildtype and A30P) did not induce α-synuclein aggregates within the 48 hr time frame examined.

To determine the effect of increasing the duration of exposure to iron on aggregation of α-synuclein at lower doses of iron, BE-M17 cells which are over-expressing A53T or wildtype α-synuclein were exposed to $FeCl_2$ for 4 days. Under these conditions, doses as low as 0.3 µM $FeCl_2$ produced detectable aggregation of α-synuclein in cells expressing A53T α-synuclein. Interestingly, these longer conditions also induced aggregation of wild type α-synuclein. In contrast, no aggregation of actin was observed, which suggests that aggregation is selective for α-synuclein.

To determine how the pattern of α-synuclein aggregation in the BE-M17 cells compares to that occurring in human brain, the response of α-synuclein in human cortical brain homogenates (from a neurologically normal donor) to iron exposure was performed, in vitro. The pattern of α-synuclein aggregation in the membrane fraction of the cortical brain homogenate following treatment for 24 hrs with 500 µM dopamine, 10 mM $FeCl_2$ and protease inhibitors (dopamine was added as an oxidant, as described below) was similar to that seen in the BE-M17 cells. This suggests that α-synuclein in BE-M17 cells and in human brain exhibit similar aggregation patterns in response to iron, and both share a strong tendency to aggregate. Further, it was observed that higher molecular weight α-synuclein immunoreactivity occasionally appeared in separating gels of immunoblots of α-synuclein cell lysates from cells grown under basal conditions. However, aggregates that migrated in the stacking gel only occurred after treatment with iron and were never observed in any of the cell lines under basal conditions. This supports prior work done with recombinant α-synuclein in vitro indicating that the mutant forms of α-synuclein have a strong tendency to oligomerize [Conway, K A, et al., PNAS USA, 97:571-576 (2000)]. However, migration of aggregates in the stacking gel might be a stricter test of aggregate formation than migration in the separating gel.

Studies showed that iron might promote protein aggregation by increasing free radical formation through the Fenton reaction [Wolozin, B., et at., Arch. Neurol. 57:793-796 (2000)]. If so, adding free radical generators, such as hydrogen peroxide or dopamine, along with the iron might increase the amount of α-synuclein aggregation. To further determine that oxidation enhanced iron-induced aggregation of α-synuclein, BE-M17 cells over-expressing A30P or wildtype α-synuclein were treated for 48 hrs with 10 mM $FeCl_2$ plus varying concentrations of dopamine (0.5, 50, and 500 µM). Cells were used to express A30P or wild type α-synuclein over 48: hrs because they do not form aggregates under these conditions, unlike cells over-expressing A53T α-synuclein. As expected, BE-M17 cells over-expressing A30P or wild type α-synuclein treated with 10 mM $FeCl_2$ alone did not induce any aggregation. Similarly, treatment with 5, 50 or 500 µM dopamine alone did not induce formation of large α-synuclein aggregates that migrate in the stacking gel. However, combining 10 mM $FeCl_2$ with 50 or 500 µM dopamine induced formation of large α-synuclein aggregates. These data show that the combination of oxidants and iron can exert additive effects on α-synuclein aggregation.

Two separate experiments indicated that the aggregation observed was a general property of α-synuclein, rather than an artifact resulting from use of clonal cell lines. BE-M17 cells that were transiently transfected with A53T α-synuclein cDNA and then treated with 10 mM $FeCl_2$ plus 100 µM $H_2O_2$ for 72 hrs developed aggregates similar to those seen in the BE-M17 cell lines stably over-expressing α-synuclein In addition, primary rat cortical neurons also showed a strong tendency to develop aggregates, requiring only 60 hrs of treatment with 0.1 mM $FeCl_2$ and 50 µM dopamine to induce formation of aggregates. Thus, the aggregation was a result of a biophysical property of α-synuclein, rather than being an artifact specific to particular clonal cell lines.

Example 2

A53T and A30P α-Synuclein Aggregates Contain Ubiquitin

In PD, Lewy bodies have also been shown to contain large amounts of ubiquitin [Dickson, D., et al., *Brain Path.,* 9:721-32 (1999); Gibb, W., et al., *J. Neurol. Neurosurg. and Psych.* 51:745-52 (1988)]. To determine whether aggregation of ubiquitin also occurred along with α-synuclein aggregation, lysates (membrane fractions) were taken from the BE-M17 cells expressing A30P α-synuclein that had been treated with $FeCl_2$ and dopamine (see Example 1, 48 hr treatment), and were immunoblotted with anti-ubiquitin antibody. The ubiquitin aggregates that accumulated under these conditions stained strongly for ubiquitin. Aggregates that accumulated in cells expressing A53T α-synuclein or wild type α-synuclein after being treated with either $FeCl_2$ alone, $FeCl_2$ plus hydrogen peroxide or $FeCl_2$ plus dopamine also contained ubiquitin. The amount of aggregated ubiquitin generally paralleled the amount of α-synuclein. The presence of ubiquitin in aggregates did not appear to result from increased ubiquitin expression because immunoblots of total lysates showed that the total amount of ubiquitin and actin was not significantly different between cell lines over-expressing α-synuclein and control cells. These data show that aggregates of α-synuclein that form in neurons in response to iron treatment are ubiquinated.

Example 3

α-Synuclein Aggregates Form Visible Inclusions Evident by Thioflavine-S Histochemistry and Electron Microscopy Thioflavine-S histochemistry and electron microscopy were used to examine the aggregates that formed in response to treatment with iron and hydrogen peroxide. Cells from each line (BE-M17: untransfected, wild type, A30P and A53T a.-synuclein) were treated with 10 mM $FeCl_2$ or 10 mM $FeCl_2$ plus 100 µM $H_2O_2$ for 72 hrs to induce formation of α-synuclein positive inclusions. The aggregates that formed were observed to bind thioflavine-S, which indicates the presence of β-pleated sheet structures. The size and number of thioflavine-S-positive aggregates paralleled the results seen by immunoblotting. The wildtype, A30P and A53T α-synuclein cell lines each showed significant accumulations of protein aggregates after treatment for 72 hrs with. 10 mM $FeCl_2$ plus 100 µM $H_2O_2$. In contrast, the untransfected line showed no accumulation of thioflavine-S positive aggregates. When only 10 mM $FeCl_2$ was used to treat the cells, thioflavine-S positive inclusions were observed only in A53T α-synuclein expressing cells. Electron microscopy was used to examine the aggregates. Cells that express A53T α-synuclein or express empty vector were treated with 10 mM $FeCl_2$ plus 100 µM $H_2O_2$ for 72 hrs and then prepared for electron microscopy. Cytoplasmic inclusions were apparent in the A53T-expressing cells, but not in the vector-transfected cells. The inclusions contained mixtures of fibrillar and amorphous material. The fibrils had an approximate diameter of 10 nm and a length of up to 10 µm. Although treatment with 10 mM $FeCl_2$ and 100 µM hydrogen peroxide was toxic to many cells, some cells containing aggregates had both fibrillar deposits and organelles that were intact, which suggests that aggregation can occur in living cells. The presence of both fibrillar and amorphous material in the aggregates has been observed in aggregates present in transgenic animals over-expressing α-synuclein [Feany, MB, et al., *Nature* 404:394-8 (2000); Masliah, E., et al., *Science* 287:1265-1269 (2000)].

Example 4

α-Synuclein Aggregates Form Visible Inclusions Evident by Immunohistochemistry

Inclusion formation was tested by immunocytochemistry. Cells that express A53T α-synuclein were treated with 10 mM $FeCl_2$ plus 100 µM $H_2O_2$ for 72 hrs, fixed and then examined with antibodies to ubiquitin and α-synuclein using peroxidase immunohistochemistry. Peroxidase staining was used because fluorescent chromagens, such as FITC or rhodamine, exhibited strong non-specific binding to the cells due to the treatment with iron. Immunohistochemistry with both the anti-α-synuclein and anti-ubiquitin antibodies showed uniform staining throughout the cytoplasm of the cells under basal conditions. Following treatment with 10 mM $FeCl_2$ plus 100 µM $H_2O_2$ for 72 hrs, the staining became less uniform. Cells stained with anti-α-synuclein antibody often displayed several large darkly stained reactive foci and multiple, small punctuate foci in each cell. Staining with ubiquitin was also present but showed fewer foci per cell. Immunocytochemistry performed with the pre-immune rabbit serum instead of primary antibody showed no reactivity under either basal or treated conditions.

Example 5

α-Synuclein Aggregation Occurs in Viable Cells

To determine the toxicity effect of $FeCl_2$ to the cell, and the relationship between α-synuclein aggregation and cell death, aggregate formation and cell viability in the presence of high and low concentrations of $FeCl_2$ was performed. As described above (Examples 3 & 4), treatment with 10 mM $FeCl_2$ plus 100 µM $H_2O_2$ for 72 hrs induced, in most non-transfected cells, formation of α-synuclein aggregates. Accordingly, these conditions also killed most of the cells (>90% cell death).

In contrast, A53T-expressing BE-M17 cells treated with 0.3 mM $FeCl_2$ plus 100 µM $H_2O_2$ for 96 hrs exhibited much less toxicity, yet still formed α-synuclein aggregates. Parallel sets of cells were processed for immunocytochemistry with antibodies to α-synuclein (SC1) and ubiquitin, or processed to measure viability using the trypan blue exclusion assay. Untreated cells showed little toxicity with 3.7±1.0% being permeable to trypan blue. The small amount of cell death present might have been caused by the trypsinization/trituration step used to dislodge the cells. Treatment with 0.3 mM $FeCl_2$ plus 100 μM $H_2O_2$ killed some cells (12.1±2.3% trypan blue positive), but the large majority of cells (87.9%) remained viable. Immunocytochemistry with anti-α-synuclein antibody showed that 21.0±3.5% of the cells had visible aggregates. Immunocytochemistry with anti-ubiquitin antibody suggested that the aggregates could contain ubiquitin, and that the aggregates contained material that had a β-pleated sheet structure that stained with thioflavine-S. Interestingly, diffuse thioflavine-S reactivity was also evident in these cells, suggesting that dispersed 'micro-aggregates' of α-synuclein might also form under the mild conditions.

Thus, the α-synuclein aggregates that formed under mild conditions reacted with the same antibodies and stains as aggregates that formed under harsher conditions. Moreover, the observation that the percentage of cells displaying α-synuclein aggregates was greater than the percentage of cells showing evidence of death suggests that many of the cells developing α-synuclein aggregates are viable.

The observation that aggregation of α-synuclein can occur in viable cells also suggests that aggregation of α-synuclein precedes cell death.

Example 6

Over-Expression of α-Synuclein Increases Free-Radical Mediated Toxicity

Despite the fact that α-synuclein aggregates can form in viable cells, it is possible that aggregation of α-synuclein might represent an initial step in the induction of toxicity. The previous results showed that α-synuclein was toxic to some cells when transiently over-expressed (Ostrerova, N., et al., *J. Neurosci.*, 19:5782-91 (1999)]. However, α-synuclein is not acutely toxic to all cells, such as BE-M17 cells. α-Synuclein is tolerated well enough to allow over-expression in transgenic animals (Feany, MB, et al., *Nature* 404:394-8 (2000); Masliah, E., et al., *Science* 287: 1265-1269 (2000)]. Although α-synuclein is not acutely toxic to BE-M17 cells under basal conditions, it was possible that α-synuclein might be toxic under other conditions, such as conditions linked to formation of aggregates.

To determine if the conditions that produce α-synuclein aggregation also produce toxicity, the vulnerability of each cell line to iron and/or hydrogen peroxide-mediated toxicity was tested. Each cell line (untransfected, wild type, A53T and A30P α-synuclein) was treated with varying doses of $FeCl_2$, $H_2O_2$ or $FeCl_2+H_2O_2$ and the amount of toxicity was determined by MTT assay. BE-M17 cells over-expressing all forms of α-synuclein showed increased vulnerability to iron-mediated toxicity (FIG. 1A). Over-expression of A53T α-synuclein had the greatest effect on toxicity, reducing the $LD_{50}$ of $FeCl_2$ over 75% (FIG. 1A). Over-expression of A30P or wild type α-synuclein constructs reduced the $LD_{50}$ values by ~50%, although the amount of toxicity seen in A30P-expressing cells in response to low levels of iron was generally greater than toxicity seen with wildtype α-synuclein (FIG. 1A). To confirm that over-expression of α-synuclein increased the vulnerability of the neuroblastoma cells to iron, iron-induced toxicity was tested using a LDH assay (FIG. 1B). The LDH assay confirmed that over-expression of the α-synuclein constructs increases iron-induced toxicity (FIG. 1B).

Figure 1C:
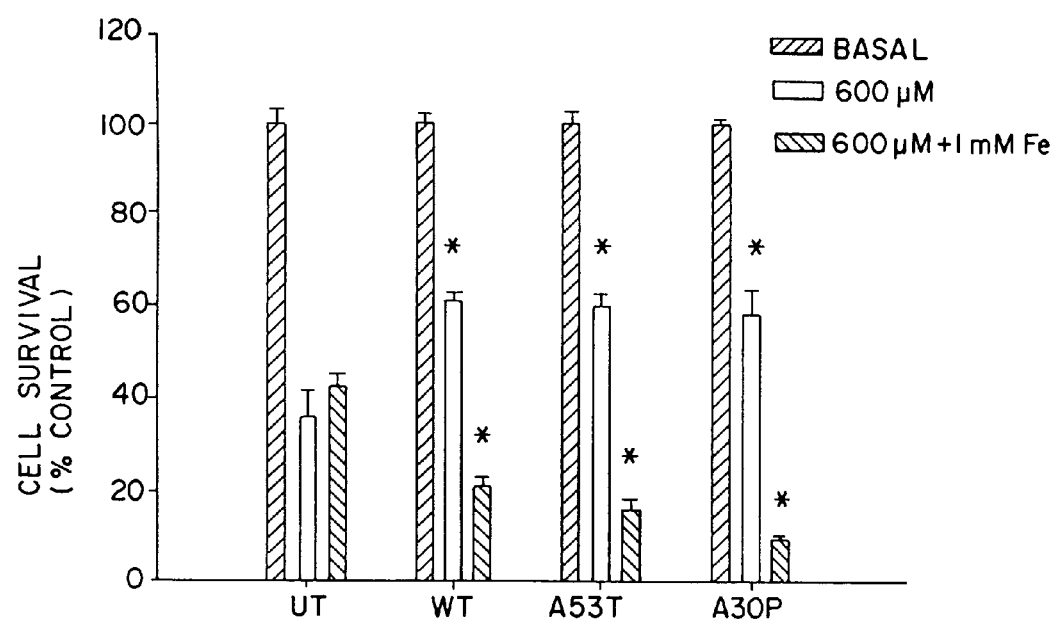
FIG. 1: α-Synuclein increases iron dependent toxicity.

MTT assays of cell lines over-expressing α-synuclein (wildtype, A53T or A30P) also revealed increased toxicity after treatment with $FeCl_2+H_2O_2$ (FIG. 1C, dark gray bars). Interestingly, over-expressing α-synuclein (wildtype, A53T or A30P) did not increase the vulnerability to $H_2O_2$ alone, and conferred modest protection to the neuroblastoma cells (FIG. 1C). These data demonstrated that increased levels of either wildtype or mutant α-synuclein can be toxic to neurons grown in cell culture under selective conditions. The data suggest that α-synuclein renders the cells particularly vulnerability to iron-mediated toxicity. The selective vulnerability to iron could result from a tendency of α-synuclein to sequester iron in α-synuclein aggregates.

Untransfected or A53T-α-synuclein expressing BE-M17 cells were treated with 10 mM $FeCl_2$ and 100 uM $H_2O_2$ for 48 hrs, then were fixed and stained for iron. The cells expressing A53T α-synuclein had much higher iron content than the untransfected cells after treatment. Sequestration of iron due to α-synuclein would increase free radical production via the Fenton reaction, particularly in cells exposed to free radical generators, such as hydrogen peroxide or dopamine. However, in the absence of iron, no Fenton reaction occurs and the α-synuclein is innocuous.

Example 7

Iron Binds to α-Synuclein

Because iron binds to other proteins that form aggregates and iron is known to accumulate in Parkinson's disease, iron might bind directly to α-synuclein. To confirm this hypothesis, the interaction of iron with α-synuclein was tested using tyrosine fluorescence as an indicator of iron binding. High doses of iron (>10 mM) will quench tyrosine fluorescence, however proteins that bind iron exhibit quenching at much lower doses (presumably because the iron is kept near the tyrosine by the protein binding). Fluorescence of tyrosine has been used to monitor binding of metals to β-amyloid [Garzon-Rodriguez W. et al., *Bioorg. Med. Chem. Let.*, 9:2243-2248 (1999), which is hereby incorporated by reference]. A similar approach was taken to analyze binding of iron to α-synuclein. Tyrosine has a fluorescence emission spectrum that has a peak emission of 310 nm when excited at 280 nm, respectively (FIG. 2A). It was observed that binding of iron reduced the fluorescence of the tyrosines in α-synuclein. The result demonstrated that it is due to specific binding to α-synuclein, because incubation of free tyrosine with similar doses of $FeCl_2$ produces no quenching. Using the Prism program (GraphPad, San Diego, Calif.) to analyze the binding curves, we observed that the data fit to a sigmoidal curve, with an $IC_{50}=173$ μM. The Hill coefficient was 1.0 ($R^2=1.0$, $P<0.0001$), indicating one binding site for iron with no cooperativity (FIGS. 2A & B). α-Synuclein was also tested for binding to other metals, including $CuCl_2$, $ZnCl_2$ and $MgCl_2$. Because the C-terminus of α-synuclein has a region with 7 glutamates and 4 aspartates, which together could chelate iron, we created a deletion construct lacking the last 27 amino acids on α-synuclein and analyzed binding of this construct. A C-terminal deletion construct of α-synuclein $AC_{1-113}$ showed over a 4-fold reduction in iron binding, with an $IC_{50}=726$ μM ($P<0.001$) (FIG. 2B). This suggests that α-synuclein binds to iron, and that the C-terminus contributes to iron-binding, but is not required for iron binding.

Example 8

Magnesium Protects Against Synuclein Aggregation

To monitor the binding profiles of Fe(II) and Mg(II) to α-synuclein in vitro we used changes of tyrosine fluorescence. Tyrosine fluorescence is used as an indicator of changes in protein conformation or binding of metals. Excitation of tyrosine at 280 nm elicits fluorescence that peaks at 310 nm for monomeric tyrosine, and at 350-400 nm for tyrosinate or dimeric tyrosine. The fluorescence spectrum of α-synuclein yielded fluorescence peaks at 310 and 400 nm. The peak at 400 nm cannot be explained by the presence of dimeric tyrosine, due to dimerization of α-synuclein, because dimerization of α-synuclein decreases the fluorescence at 400 nm, and tends to eliminate the peak at 400 nm. Moreover, gel electrophoresis and mass spectrometry of the α-synuclein showed that the α-synuclein was monomeric. This suggests that the peak at 400 nm is due to tyrosinate, which could result from proton transfer from the phenolic hydroxyl to aspartic or glutamic acid protein acceptors. Incubating α-synuclein with increasing doses of Fe(II) rapidly reduced the fluorescence of tyrosines in α-synuclein at both 310 and 400 nm. Plotting of the fluorescence quenching showed a sigmoid curve, with an $IC_{50}=173$ μM and a Hill coefficient of 1.0 ($R^2=1.0$, $P<0.0001$), indicating one binding site or multiple binding sites with the same affinity and no cooperativity. The actual affinity of iron for α-synuclein could be below 173 μM because tyrosine fluorescence is a better indicator of conformation changes than absolute affinity.

The effect of magnesium on α-synuclein differed dramatically from that of iron. Magnesium increased the fluorescence at 400 nm but did not affect the fluorescence at 310 nm. Binding of magnesium to α-synuclein was also striking because the tyrosine fluorescence showed a sharp stepwise increase between 60 and 80 uM of magnesium indicating cooperative binding. The cooperative regulation of tyrosine fluorescence, specifically at 400 nm, suggests that magnesium causes a conformational change in synuclein differing from that induced by iron. Co-incubating magnesium with iron did not prevent iron-induced quenching of α-synuclein tyrosine fluorescence suggesting that iron and magnesium bind to different sites on α-synuclein.

We also examined how the A53T mutation in human α-synuclein affected binding of iron and magnesium. The A53T mutation did not change the apparent affinity of iron for α-synuclein, but did abolish the interaction between magnesium and α-synuclein. Previous studies have shown that A53T mutation changes the conformation of α-synuclein by increasing its helical content (Polymeropoulos et al, *Science*, 276:2045-7(1997)). These conformational changes might also reduce binding of magnesium to α-synuclein.

Knowing that magnesium and iron induce opposing changes in α-synuclein tyrosine fluorescence, it is believed that binding of magnesium might convert α-synuclein to a conformation that resists aggregation perhaps by preventing β-pleated sheet formation. To test this, wildtype recombinant α-synuclein was incubated with 0-3 mM $FeCl_2$ and 0 or 100 μM $MgCl_2$ for 24 hrs at 37° C., then immunoblotting was performed for α-synuclein and quantified aggregation by video densitometry. We observed a striking reduction in formation of high molecular weight aggregates of α-synuclein at all but the highest dose of iron (n=3, $P<0.0001$). Analyses using thioflavine-S to measure aggregation of recombinant α-synuclein also showed induction of α-synuclein aggregation by iron and inhibition of aggregation by magnesium under similar conditions. In separate experiments, we observed that magnesium also inhibited spontaneous aggregation of α-synuclein.

Since we did not observe interaction between magnesium and A53T α-synuclein using tyrosine fluorescence, we tested whether aggregation of recombinant A53T α-synuclein was also insensitive to magnesium. We incubated recombinant A53T α-synuclein with 0-3 mM $FeCl_2$ and 0 or 100 μM $MgCl_2$ for 24 hrs, then immunoblotted the α-synuclein and quantified aggregation by video densitometry. We observed that magnesium was unable to inhibit iron-induced aggregation of A53T α-synuclein. The inability of magnesium to inhibit aggregation of A53T α-synuclein is consistent with the tyrosine fluorescence data suggesting that magnesium does not interact with A53T α-synuclein.

The ability of magnesium to inhibit aggregation of wild-type α-synuclein in vitro suggests that it might also be able to inhibit aggregation in living neurons. To test this, the inventors examined the ability of magnesium to inhibit α-synuclein aggregation in primary cortical neurons grown in cell culture. Primary cortical neurons were treated with 1 mM $FeCl_2$ plus 0-1.5 mM $MgCl_2$ for 3 days, the α-synuclein was immunoblotted and the amount of aggregate determined by video densitometry. Treatment with increasing doses of magnesium from 0.2 to 1.5 mM produced dose-dependent reduction in formation of high molecular weight α-synuclein aggregates. Doses as low as 0.5 mM of magnesium produced statistically significant reduction in formation of α-synuclein positive aggregates. Magnesium exerted a similar aggregation-inhibiting effect on BE-M17 neuroblastoma cells over-expressing wild type α-synuclein. In contrast, magnesium was unable to inhibit aggregate formation in BE-M17 cells expressing the human A53T α-synuclein cDNA, which is consistent with a hypothesis that magnesium inhibits α-synuclein aggregation by binding to α-synuclein, inducing a conformational change.

The inventors also examined the amount of aggregates present using an antibody to ubiquitin. As set forth previously, the accumulation of high molecular weight ubiquitin adducts correlates with the formation of α-synuclein aggregates. Primary cortical neurons were treated as described above and the aggregates were immunoprecipitated with anti-α-synuclein antibody and immunoblotted with anti-ubiquitin antibody. An increase in ubiquitination of α-synuclein upon treatment with 0.3 mM iron and 50 μM dopamine for 3 days was observed. However, treating the cells with magnesium produced a statistically significant decrease in ubiquitin immunoreactivity with doses as low as 0.5 mM (n=3, $P<0.0001$). Thus, magnesium inhibits formation of ubiquitin positive α-synuclein aggregates in primary neurons.

Next, whether magnesium also prevents formation of α-synuclein-positive inclusions in BE-M17 neurons stably over-expressing wildtype α-synuclein was investigated. The neurons were treated with 1 mM $FeCl_2$ plus 50 μM dopamine plus 0 or 1 mM $MgCl_2$ for 3 days, and then examined by immunocytochemistry using anti-α-synuclein and anti-ubiquitin antibodies. Neurons treated with iron and dopamine showed abundant α-synuclein-positive inclusions, whereas neurons treated with iron, dopamine and magnesium showed little accumulation of α-synuclein—positive inclusions.

Magnesium-induced inhibition of α-synuclein aggregation also correlated with neuroprotection, as measured by the MTT assay. BE-M17 neuroblastoma cells stably transfected with vector or wildtype α-synuclein were treated with $FeCl_2$ plus dopamine plus 0 or 0.8 mM $MgCl_2$ for 2 days, and then viability was analyzed by the MTT assay (the doses were chosen to optimize optical densities for the MTT assay). The cell line over-expressing wildtype α-synuclein showed increased toxicity in response to the iron/dopamine treatment, which is consistent with the observations above. Treatment with magnesium increased cell survival 2.4-fold in the wildtype cell line but only 1.3-fold in the control cell line (compared to survival among cells treated with $Fe^{2+}$/dopamine alone). This suggests that the cell line with more α-synuclein-related toxicity had correspondingly more protection by magnesium.

How magnesium affected neurons from the central nervous system was also examined. Primary cultures of cortical neurons were treated with 0.3 mM $FeCl_2$ plus 50 μM dopamine plus 0-2 mM $MgCl_2$ for 3 days (a relatively low dose of iron was used to enable quantitation of neuronal processes). To quantify the amount of neuroprotection provided by magnesium, the percent of processes longer than 100 μm as a characteristic of cell viability was determined. Treating with iron plus dopamine lead to blunting of neuronal processes, reducing the number of neuronal processes over 100 μl by about 60% (n=5, P<0.001). Inclusions also formed in these neurons. However, neurons treated with iron, dopamine, and 1-2 mM magnesium showed only a 20% loss of processes, and did not exhibit any formation of α-synuclein-positive inclusions. These results are consistent with previous studies, indicating that magnesium is cytoprotective (Beal, M. F., *Ann. Neurol.* 31:119-30 (1992)). Furthermore, these results indicate that magnesium can prevent α-synuclein aggregation in neurons of the central nervous system as well as in neuronal cell lines.

Figure 3B:
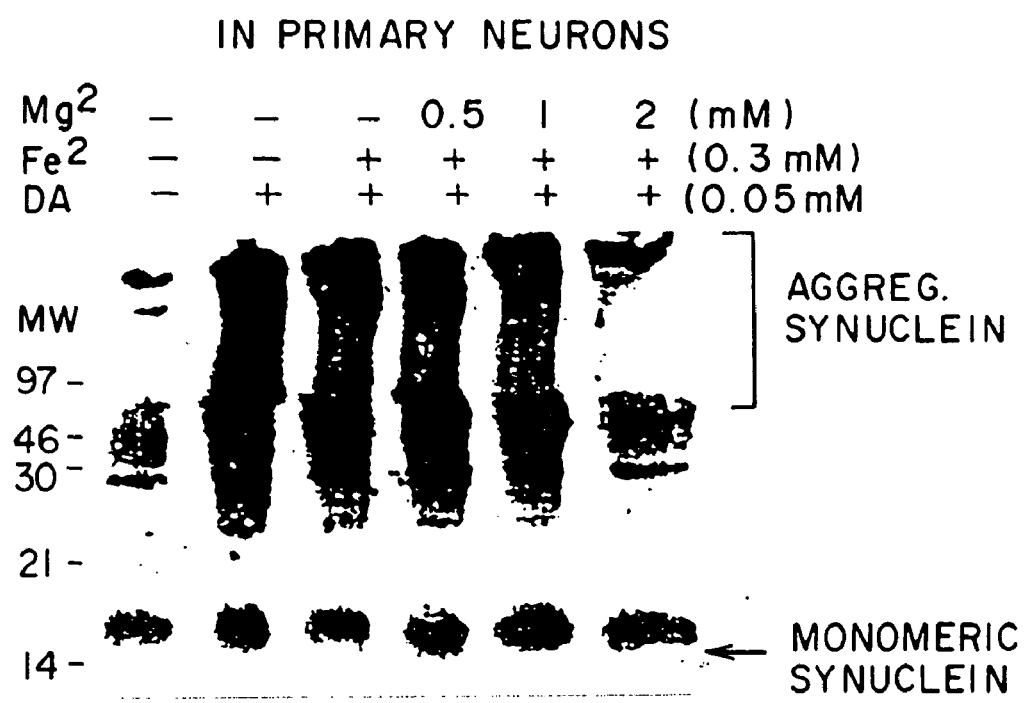

In summary, magnesium inhibited both spontaneous and iron-induced aggregation (FIG. 3). This could occur because binding of magnesium to α-synuclein converts α-synuclein to a conformation that resists aggregation (FIG. 3B).

Interestingly, the dose at which magnesium exerts its anti-aggregating effects is similar to the therapeutic dose used to treat pre-eclampsia, for example. These doses of magnesium are therapeutically achievable. This could occur because binding of magnesium to α-synuclein converts α-synuclein to a conformation that resists aggregation (FIG. 3B).

Example 9

Identification of Anti-α-Synuclein Peptides

Phage display (phage display kit was from New England Biolabs (Beverly, Mass.)) was used to specifically select for peptides that can inhibit iron binding. Phages were identified from libraries that bind to amino acids 121-131 and amino acids 61-87 of α-synuclein and partially inhibit iron-induced aggregation of α-synuclein. The peptides were selected using the α-synuclein 121-131 and 61-87 peptides as the bait. One such peptide has the sequence SLKRLPK (SEQ ID NO: 7).

To demonstrate that the peptide SLKRLPK (SEQ ID NO: 7) binds α-synuclein, the α-synuclein was absorbed to a plastic well, phage was added at dilutions of 1: 10, 1: 100, and 1: 1000, incubated 1 hour and washed 5 times. Bound phage was detected by adding peroxidase coupled anti-phage antibody, incubating 1 hr, washing 5 times and detecting signal using the peroxidase substrate ABTS. Bound phage produces a dark green signal that is measured as optical density with a spectrophotometer. Using these conditions, the phage containing the SLKRLPK (SEQ ID NO: 7) peptide gave OD's of 0.882, 0.844, and 0.480 at dilutions of 1: 10, 1: 100, and 1: 1000, respectively. By contrast, another phage that did not bind gave OD's of 0.019, -0.027, and -0.554 respectively.

This peptide was also tested for its ability to inhibit iron-induced α-synuclein aggregation in vitro. A 10-fold excess of the peptide was able to inhibit α-synuclein aggregation by 38%, as determined by densitometric quantification. This level of inhibition is extremely significant, given that if this were to translate into a 38% reduction in vivo it could slow the progression of PD by several years.

The peptide has the sequence "SLKRLPK" (SEQ ID NO: 7), and corresponds to a sequence expressed by a phage that shows particularly strong binding to α-synuclein by ELISA. The sequence does not contain tyrosines or tryptophans that can add to the fluorescence and complicate the analyses. This phage was generated before we understood the importance of iron for α-synuclein biochemistry (hence, the binding site was not specifically targeted against iron binding). Even so, incubating a 10-fold excess of peptide with α-synuclein reduces iron-induced α-synuclein aggregation by 38%.

We claim:

1. An isolated peptide that will bind to α-synuclein and inhibit aggregation of α-synuclein, said peptide consisting of a sequence selected from: WRQTRKD (SEQ ID NO:1); HYAKNPI (SEQ ID NO:2); ATINKSL (SEQ ID NO:3); RRRGMAI (SEQ ID NO:4); TKHGPRK (SEQ ID NO:6); SLKRLPK (SEQ ID NO:7); RLRGRNQ (SEQ ID NO:8); WPFHHHR (SEQ ID NO:9); HLYHHKT (SEQ ID NO:10); THIHHPS (SEQ ID NO:11); or MMMMMRL (SEQ ID NO:12).

2. The peptide of claim 1, wherein the peptide is SLKRLPK (SEQ ID NO:7), THIHHPS (SEQ ID NO:11), or MMMMMRL (SEQ ID NO:12).

3. The peptide of claim 2, which is SLKRLPK (SEQ ID NO:7).

4. A composition comprising a peptide of claim 1, and a pharmaceutically acceptable carrier.

5. The composition of claim 4, wherein the peptide is SLKRLPK (SEQ ID NO:7), THIHHPS (SEQ ID NO:11), or MMMMMRL (SEQ ID NO:12).

6. The composition of claim 5, wherein the peptide is SLKRLPK (SEQ ID NO:7).

7. A method for treating a neurodegenerative disease that involves the formation of Lewy bodies, comprising administering to a patient in need thereof one or more of the peptides according to claim 1, whereby the presence of Lewy bodies remains the same or is reduced.

8. The method of claim 7, wherein the one or more peptides is selected from:
SLKRLPK (SEQ ID NO:7); THIHHPS (SEQ ID NO:11); or MMMMMRL (SEQ ID NO:12).

9. The method of claim 7, wherein the peptide is SLKRLPK (SEQ ID NO:7).

10. The method of claim 7, wherein the neurodegenerative disease is Parkinson's disease (PD), Alzheimer's disease (AD) diffuse Lewy body disease, mixed AD-PD, multiple system atrophy or Hallervorden-Spatz disease.

11. The method of claim 7, wherein the neurodegenerative disease is Parkinson's disease.

12. A method for inhibiting the formation of aggregates of α-synuclein, comprising treating the α-synuclein with a peptide according to claim 1.

* * * * *

SEQUENCE LISTING

<160> NUMBER OF SEQ ID NOS: 12

<210> SEQ ID NO 1
<211> LENGTH: 7
<212> TYPE: PRT
<213> ORGANISM: Homo sapiens

<400> SEQUENCE: 1

Trp Arg Gln Thr Arg Lys Asp
1               5

<210> SEQ ID NO 2
<211> LENGTH: 7
<212> TYPE: PRT
<213> ORGANISM: Homo sapiens

<400> SEQUENCE: 2

His Tyr Ala Lys Asn Pro Ile
1               5

<210> SEQ ID NO 3
<211> LENGTH: 7
<212> TYPE: PRT
<213> ORGANISM: Homo sapiens

<400> SEQUENCE: 3

Ala Thr Ile Asn Lys Ser Leu
1               5

<210> SEQ ID NO 4
<211> LENGTH: 7
<212> TYPE: PRT
<213> ORGANISM: Homo sapiens

<400> SEQUENCE: 4

Arg Arg Arg Gly Met Ala Ile
1               5

<210> SEQ ID NO 5
<211> LENGTH: 7
<212> TYPE: PRT
<213> ORGANISM: Homo sapiens

<400> SEQUENCE: 5

Thr His Arg Leu Pro Ser Arg
1               5

<210> SEQ ID NO 6
<211> LENGTH: 7
<212> TYPE: PRT
<213> ORGANISM: Homo sapiens

<400> SEQUENCE: 6

Thr Lys His Gly Pro Arg Lys
1               5

<210> SEQ ID NO 7
<211> LENGTH: 7
<212> TYPE: PRT
<213> ORGANISM: Homo sapiens

<400> SEQUENCE: 7

Ser Leu Lys Arg Leu Pro Lys
1               5

<210> SEQ ID NO 8
<211> LENGTH: 7
<212> TYPE: PRT
<213> ORGANISM: Homo sapiens

<400> SEQUENCE: 8

Arg Leu Arg Gly Arg Asn Gln
1               5

<210> SEQ ID NO 9
<211> LENGTH: 7
<212> TYPE: PRT
<213> ORGANISM: Homo sapiens

<400> SEQUENCE: 9

Trp Pro Phe His His His Arg

```
<210> SEQ ID NO 10
<211> LENGTH: 7
<212> TYPE: PRT
<213> ORGANISM: Homo sapiens

<400> SEQUENCE: 10

His Leu Tyr His His Lys Thr
1               5

<210> SEQ ID NO 11
<211> LENGTH: 7
<212> TYPE: PRT
<213> ORGANISM: Homo sapiens

<400> SEQUENCE: 11

Thr His Ile His His Pro Ser
1               5

<210> SEQ ID NO 12
<211> LENGTH: 7
<212> TYPE: PRT
<213> ORGANISM: Homo sapiens

<400> SEQUENCE: 12

Met Met Met Met Met Arg Leu
1               5
```